(12) United States Patent
Guizzardi et al.

(10) Patent No.: US 9,179,942 B2
(45) Date of Patent: Nov. 10, 2015

(54) HOLDING DEVICE HAVING A LONGILINEAL ELEMENT ADAPTED FOR MAINTAINING A PREDETERMINED INTERVERTEBRAL SPACING

(75) Inventors: Giancarlo Guizzardi, Florence (IT); Frédéric Bardel, Houplines (FR); Guy Deneuvillers, Merlimont (FR)

(73) Assignee: COUSIN BIOTECH, Wervicq Sud (FR)

( * ) Notice: Subject to any disclaimer, the term of this patent is extended or adjusted under 35 U.S.C. 154(b) by 47 days.

(21) Appl. No.: 13/697,937

(22) PCT Filed: May 10, 2011
(Under 37 CFR 1.47)

(86) PCT No.: PCT/FR2011/051048
§ 371 (c)(1),
(2), (4) Date: Mar. 28, 2013

(87) PCT Pub. No.: WO2011/161341
PCT Pub. Date: Dec. 29, 2011

(65) Prior Publication Data
US 2013/0204303 A1    Aug. 8, 2013

(30) Foreign Application Priority Data

Jun. 23, 2010   (FR) ...................................... 10 55017

(51) Int. Cl.
*A61B 17/70*    (2006.01)
(52) U.S. Cl.
CPC ......... *A61B 17/7053* (2013.01); *A61B 17/7062* (2013.01)

(58) Field of Classification Search
CPC ........... A61B 17/7053; A61B 17/7062; A61B 17/7064; A61B 17/7065; A61B 17/7067; A44B 11/02; A44B 11/10; A44B 11/18
USPC ............. 606/246, 248, 263; 24/171, 194, 197
See application file for complete search history.

(56) References Cited

U.S. PATENT DOCUMENTS

| 510,358 A | * | 12/1893 | Mullane | .......................... | 24/171 |
| 688,503 A | * | 12/1901 | Cross | .......................... | 24/163 R |

(Continued)

FOREIGN PATENT DOCUMENTS

| CA | 2106808 A1 | 4/1994 |
| EP | 1343424 B1 | 9/2004 |

(Continued)

OTHER PUBLICATIONS

European Patent Office, International Search Report in International Application No. PCT/FR2011/051048, dated Jul. 12, 2011.

*Primary Examiner* — Pedro Philogene
*Assistant Examiner* — David C Comstock
(74) *Attorney, Agent, or Firm* — Kenyon & Kenyon LLP

(57) ABSTRACT

The subject matter of the present invention relates to a maintaining device suitable for maintaining a predetermined intervertebral spacing, comprising a) a slender component, which is preferably substantially flat, of predetermined main width having a first end and a second end capable of being placed around the spinous processes, b) a rigid support comprising two side parts mounted between front and rear parts, and c) a blocking component mounted so as to slide on the side parts.

15 Claims, 2 Drawing Sheets

(56) References Cited

U.S. PATENT DOCUMENTS

| | | | | |
|---|---|---|---|---|
| 1,337,965 | A * | 4/1920 | Russ | 24/171 |
| 1,611,588 | A * | 12/1926 | Hyde | 24/171 |
| 1,836,923 | A * | 12/1931 | Hodge | 24/196 |
| 2,129,872 | A * | 9/1938 | Reiter | 24/196 |
| 2,480,430 | A * | 8/1949 | Walters | 606/203 |
| 5,496,318 | A * | 3/1996 | Howland et al. | 606/249 |
| 5,609,634 | A * | 3/1997 | Voydeville | 623/13.11 |
| 5,683,404 | A | 11/1997 | Johnson | |
| 7,296,327 | B2 * | 11/2007 | Anderson et al. | 24/171 |
| 7,704,281 | B2 * | 4/2010 | Pasquet et al. | 623/17.16 |
| 8,029,541 | B2 * | 10/2011 | Alamin et al. | 606/248 |
| 2008/0015693 | A1 * | 1/2008 | Le Couedic | 623/17.11 |
| 2009/0306716 | A1 * | 12/2009 | Beger et al. | 606/249 |
| 2010/0211102 | A1 | 8/2010 | Belliard et al. | |

FOREIGN PATENT DOCUMENTS

| | | |
|---|---|---|
| FR | 2704745 B1 | 11/1995 |
| FR | 2921248 A1 | 3/2009 |
| WO | 94/26192 A1 | 11/1994 |
| WO | 2009/149407 A1 | 2/2009 |

* cited by examiner

HOLDING DEVICE HAVING A LONGILINEAL ELEMENT ADAPTED FOR MAINTAINING A PREDETERMINED INTERVERTEBRAL SPACING

CROSS REFERENCE TO RELATED APPLICATION

This is a 371 national phase application of International Application No. PCT/FR2011/051048, filed May 10, 2011, claiming priority to French application No. 10-55017, filed Jun. 23, 2010, the contents of which are incorporated herein by reference in their entirety.

The present invention relates to the technical field of holding devices which are adapted for maintaining a predetermined intervertebral spacing.

This type of holding device employs a ligament or a longilineal element capable of maintaining a predetermined intervertebral spacing during extension and flexure movements, but also in the natural spinal curvature position.

This type of longilineal element can be used alone or in combination with an intervertebral support device such as an intervertebral wedge.

Such an inververtebral support device, positioned between the spinous processes and/or the laminae, depending in particular on the condition of the natural ligaments, can contribute a shock-absorbing effect between two adjoining vertebrae.

Such longilineal elements exhibit, once their two ends are joined to form a loop capable of surrounding the spinous processes and/or the laminae of the two adjoining vertebrae, a much lower breaking strength [daN] than the breaking strength conventionally obtained in tension applied to the two free ends of the ligament.

Indeed, the method of attachment selected for joining the two ends of the longilineal element constitutes an area of weakness exhibiting lower breaking strength than that of the longilineal element.

The different systems for joining the two free ends of a longilineal element are the following:

forming a simple or double knot in the two ends of the longilineal element;

positioning one loop at one of the ends of the longilineal element so as to pass the other free end through the loop, then sewing the free end run through the loop over a portion of the longilineal element;

running the longilineal element into a complex-shaped intervertebral wedge comprising numerous individual parts such as the wedge described in EP 1,343,424;

threading one or both free ends of the longilineal element into a deformable metal ring, then compressing the ring so as to clamp the two ends together.

These systems for joining the free ends of the longilineal elements have the disadvantages that they are complex to implement during a surgical operation.

Further, they are non-reversible for the most part, and have low breaking strength compared to that of the longilineal element.

In addition, when the joining system is complex and involves numerous individual parts, there is a risk with regard to flexure and extension motions to which the two adjoining vertebrae are subjected.

Indeed, it is possible for one of the parts to become detached, which would be prohibitive in terms of use. Indeed, the implantation area, which is closest to the spinal cord, is very sensitive.

These systems also have the disadvantage that, during joining of the two ends of the longilineal element defining a loop with a given perimeter positioned around two adjoining spinous processes and/or two adjacent laminae, the tension exerted on the ends can vary and therefore alter the perimeter of the loop that is formed, thus generating inaccuracies; this is all the more true in that the joining is performed manually.

The present invention has the goal of offsetting the different aforementioned disadvantages.

To this end, the object of the present invention relates to a holding device adapted to maintain a predetermined intervertebral spacing that offsets all or part of the aforementioned problems.

More precisely, the holding device according to the present invention comprises a round or substantially flat longilineal element with principal width l, having first and second ends, capable of being positioned around spinous processes.

The holding device according to the present invention also comprises a rigid support comprising two lateral portions assembled between front and rear portions.

The first end is joined or capable of being joined to the rear portion and the second end remains free.

The holding device according to the present invention comprises a locking element mounted so as to slide on the lateral portions and defining front and rear passage areas with the front and rear portions, respectively.

This arrangement allows the second free end to pass into the rear passage area, then into the front passage area while partially wrapping around the locking element so that:

a) the portion of the longilineal element extending substantially between its first end and the locking element forms a loop with a given perimeter p; and b) the application of opposite tensions to the inner walls of the loop causes movement of the locking element toward the front portion and the locking of the longilineal element within the front passage area between the locking element and the front portion of the support.

Advantageously, the support and the locking element provide a mechanical joining of the two ends of the longilineal element because the breaking strength [daN] obtained is at least on the order of about 50%, possibly more, of the breaking strength [daN] of the longilineal element.

What is more, when the surgeon threads the second free end into the rear passage area, then into the front passage area, in order to form a loop with a given perimeter p, surrounding for example two adjoining spinous processes, the opposite forces exerted by the spinous processes during flexural motions of the vertebral column against the inner walls of the formed loop cannot lengthen the loop and alter the perimeter that was previously assigned to it by the surgeon.

This therefore makes it possible to maintain a predetermined intervertebral spacing between the two spinous processes treated. There is thus no inaccuracy during the joining of the two ends of the longilineal element for the forming of a loop.

Advantageously, the joining of the first and second ends is totally reversible by exerting a pull on the portion of the longilineal element on the periphery of the rear passage area in a direction opposite to the front passage area while holding the support.

What is more, it is possible to exert a pull on the portion of the longilineal element on the periphery of the rear passage area in order to reduce the perimeter of the loop that is formed.

The holding device according to the present invention thus makes it possible to offer reversible joining of the first and second ends of the longilineal element, as well as easy adjustment of the perimeter of the loop that is formed.

Advantageously, the longilineal element is substantially flat so that the rubbing generated by the passage of said element on the front and rear parts and the locking element participate in the locking of the longilineal element in the front and rear passage areas.

In one variant, the inner distance d separating the lateral portions is substantially on the order of that of the principal width l of said longilineal element, or less.

This arrangement makes it possible to increase the rubbing areas between the longilineal element and the front, rear, and lateral portions and the locking element in order to improve the locking of the longilineal element in the front and rear passage areas.

In one variant, the front portion of the support is sized and positioned with respect to the locking element so as to serve as a forward stop for said locking element. Preferably, the left and right edges of the front portion project on either side of the lateral portions and serve as stops on the left and right edges of the locking element.

This arrangement of the elements makes it possible to limit the tightening of the longilineal element and to make the system safe by limiting the shearing force on the longilineal element.

In one variant, the locking element includes a central opening the inner lateral edges whereof are arranged so as to accommodate the lateral portions of the support and serve as a guide for the sliding of the locking element on the lateral portions between the front and rear portions of the support.

In one variant, the upper periphery of the central opening facing the front portion is defined by the left and right edges, and the left edge projects from the upper periphery such that only the left edge of the locking element comes to bear against the front portion of the support providing play between the right edge and the front portion.

The play provided between the right edge and the front portion of the support allows the clamping force to be reduced.

This therefore makes it possible to limit the shearing force on the longilineal element clamped between the locking element and the front portion of the support when opposite tensions are exerted on the inner walls of the loop.

The breaking strength of the longilineal element, the ends whereof are joined to the support means and those of the locking element, therefore allows a higher breaking strength.

In one variant, the locking element includes vertical grooves, oriented from the rear portion toward the front portion and reaching to the upper periphery, and possibly to the lower periphery of the central opening so as to provide clamping teeth on the upper periphery, and possibly on the lower periphery.

Locking of the longilineal element in the front and rear passage areas is thus improved.

In one variant, the central opening leading toward the front portion of the support comprises, along at least one of its edges, left or right, teeth shaped like saw teeth.

Quite obviously, it will be understood that the surface of the support can be either smooth or rough to enable locking.

In one variant, the inner angular areas of the support defined between the front and/or rear portions and one or the other of the two lateral portions are rounded so as to reduce the shearing force exerted on the portions of the longilineal element that are in contact with the angular areas.

In one variant, the support is made of a material selected from among the following materials: stainless steel, titanium, ceramic, polypropylene, polyethylene, high density polyethylene, carbon fiber, polyether etherketone (PEEK), chrome-cobalt alloy, etc.

In one variant, the longilineal element is obtained by the shaping of multifilament and/or monofilament yarns by weaving, knitting or braiding, preferably by braiding of multifilament yarns.

This shaping allows the forming of textured flat surfaces that increase the friction forces generated between the longilineal element and the support and the locking element, and correlatively increase the locking of the longilineal element in the front and rear passage areas.

Moreover, multifilament yarns make it possible to increase the breaking strength of the longilineal element compared with monofilaments or solid longilineal elements.

In one variation, the longilineal element is made of a material selected from among the following materials: polypropylene, polyethylene terephtalate, polyethylene, high density polyethylene, polyamide 6-6, 4-6 or 12, polyurethane, polyether etherketone (PEEK).

In one variant, the longilineal element is a tubular braid, the first and second ends whereof have been sewn so as to flatten the tubular braid.

The longilineal element thus exhibits improved breaking strength because the tensions are exerted simultaneously on both interconnected textile layers.

In one variant, the second end is given a pointed shape; it preferably comprises a gripping loop.

In one variant, the longilineal element includes a central area positioned between the lateral areas and the lateral areas have a lower coefficient of friction than the central area in order to improve the breaking strength of the longilineal element the ends whereof are joined on the support and the locking element while still preserving the friction generated to improve the locking of the longilineal element.

Preferably, the central area is formed, preferably by braiding, from multifilament and/or monofilament yarns, of polyethylene terephthalate, of polypropylene or of polyamide while the lateral areas are formed from multifilament and/or monofilament yarns made of high density polyethylene, of polytetrafluoroethylene.

Said lateral areas can be coated with a material having a low coefficient of friction, such as silicone or PTFE.

In one variation, the device includes an intervertebral support device such as an intervertebral wedge of which at least the anterior portion is capable of being positioned between the over- and underlying laminae of the over- and underlying vertebrae respectively.

In one variant, the intervertebral support device comprises at least one attachment means for anchoring the longilineal element.

Preferably, this joining means is positioned on one of its lateral walls.

The present invention will be better understood upon reading an embodiment, mentioned without limitation, and wherein.

Figure 1A:
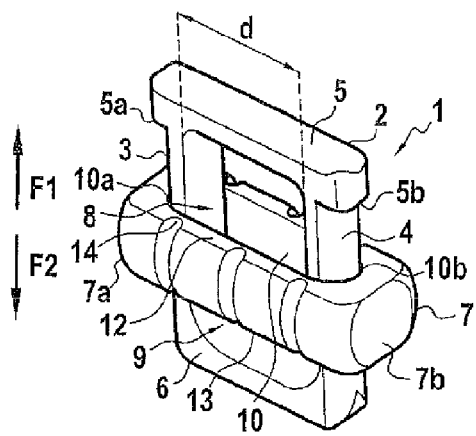
FIG. 1A is a schematic view of a first example of a support and a locking element according to the invention.

The holding device 1 partially shown in FIG. 1A includes a rigid support 2, which in this particular example takes the form of a frame.

In the example described here, the support 2 according to the present invention includes two lateral portions 3 and 4 assembled between the front 5 and rear 6 portions as well as a locking element 7 mounted so as to slide on the lateral portions 3, 4 and defining front 8 and rear 9 passage areas with the front 5 and rear 6 portions.

The lateral portions 3 and 4 are separated by an inner distance d.

The inner angular areas of the support 2 defined between the front 5 and/or rear 6 portions and one or the other of the two lateral parts 3 and 4 are rounded.

In the example described here, the front portion 5 of the support 2 is sized and positioned with respect to the locking element 7 so as to act as a forward stop for the locking element 7.

In this particular example, the left 5a and right 5b edges of the front portion 5 projecting to either side of the lateral portions 3 and 4 act as stops on the left 7a and right 7b edges of the locking element 7.

The locking element 7 also has a central opening 10 the inner lateral edges 10a and 10b whereof are so arranged as to a) accommodate the lateral portions 3 and 4 of the support 2 and b) serve as a guide for the sliding of the locking element in the directions F1 and F2 between the front 5 and rear 6 portions.

The locking element 7 includes vertical grooves 11, oriented from the rear 6 toward the front 5 portion, reaching to the upper 12 and lower 13 peripheries of the central opening 10 so as to provide clamping teeth 14.

Figure 1B:
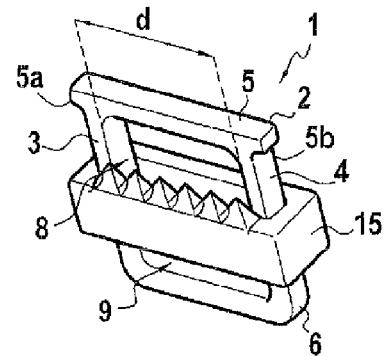
FIG. 1B is a schematic view of a second example of a support and of a locking element according to the invention.
Figure 1C:
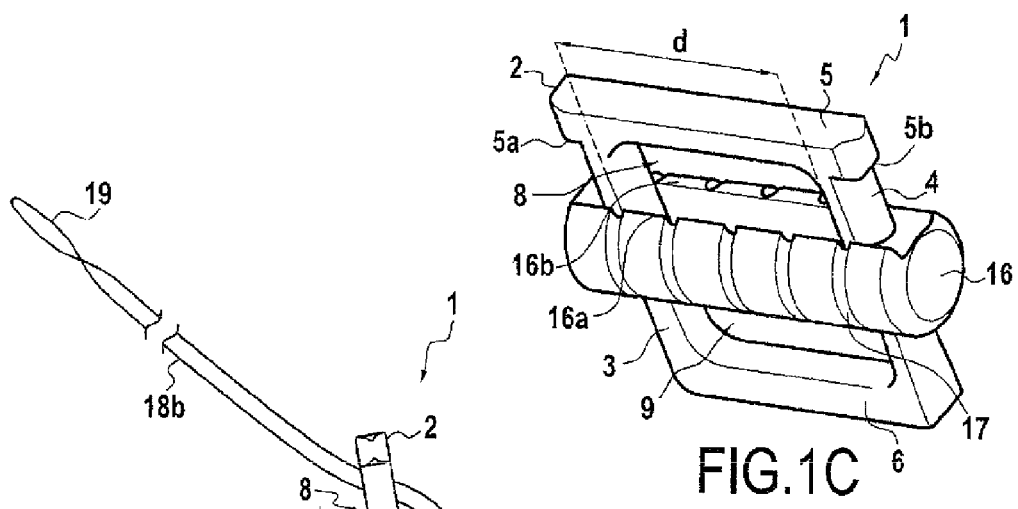
FIG. 1C is a schematic view of a third example of a support and of a locking element according to the invention.

In FIGS. 1B and 1C, only the locking elements 15 and 16 differ from the locking element 7 shown in FIG. 1A.

The locking element 15 comprises, at the central opening 10 leading to the front portion 5 of the support 2 along the left edge 15a, teeth shaped like saw teeth.

In FIG. 1C, the central opening 10 of the locking element 16 leading to the front portion 5 is defined by the left 16a and right 16b edges.

More precisely, in this example, the left edge 16a projects from the opening 10 such that only the latter comes into contact with the front portion 5 of the support 2 when the locking element 7 slides toward the front portion 5, thereby providing play between the left edge 16a and the front portion 5.

The locking element 16 includes vertical grooves 17 similar to the vertical grooves shown in FIG. 1A.

Figure 2:
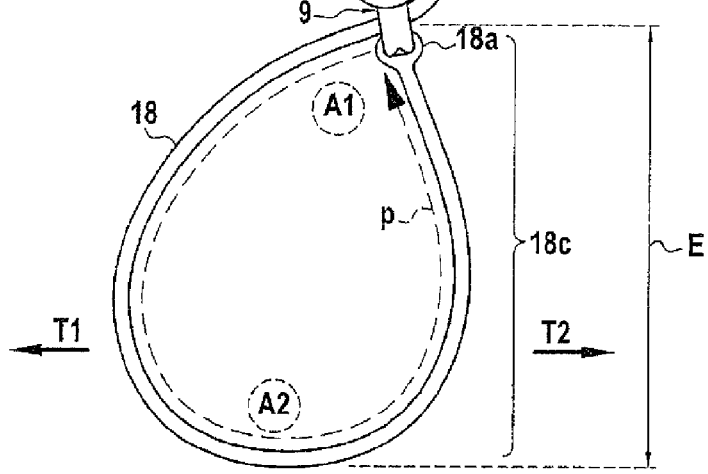
FIG. 2 is a schematic perspective view of a device for maintaining a maximum intervertebral spacing in operation, comprising the support and the locking element shown in FIG. 1C.

The holding device 1 shown in FIG. 2 includes a support 2 and a locking element 16 like those shown in FIG. 1C.

The device 1 also includes a substantially flat longilineal element 18 having a first end 18a joined to the rear portion 6 of the support 2 and a second, free end 18b comprising a gripping loop 19.

In this particular example, the longilineal element 18 is a tubular braid obtained starting with multifilament yarns and the ends whereof 18a and 18b have been sewn so as to flatten the braid.

In this particular example, the width of the longilineal element 18 is substantially on the order of the internal distance d separating the lateral portions 3 and 4 so as to provide for friction with the different parts 3, 4, 5 and 6 of the support 2 during passage through the longilineal element 18.

This arrangement thus improves the locking of the longilineal element 18.

In operation, the second free end 18b runs through the rear passage area 9, then the front passage area 8.

During this passage, the second free end 18b partially surrounds the locking element 16 so that the portion 18c of the longilineal element 18 extending substantially between the first end 18a and the locking element 16 forms a loop with a given perimeter p and maximum height E surrounding, in this particular example, the overlying A1 and underlying A2 spinous processes.

The application of opposite tensions T1 and T2 during flexure or extension motions of the vertebral column on the inner walls of the loop portion 18c causes displacement of said locking element 16 toward the front portion 5 of the support 2 and locking of the longilineal element 18 in the front passage area 8 between the locking element 16 and the front portion 5 of the support 2.

The vertical grooves 17 of the locking element 16 constitute clamping teeth which improve clamping and hence the blocking of the longilineal element 18 in the front passage area 8.

The raised left edge 16a allows the provision of play with the front portion 5 in the front passage area 8, thus decreasing the shearing force exerted on the longilineal element 18.

During an operation, the surgeon thus easily positions the holding device 1 between two portions of the vertebral column without having to exert tension during joining of the loop 18c.

What is more, this joining is reversible, and the inner perimeter p of the loop 18c, and hence the maximum spacing E, are also easily adjustable.

Figure 3:
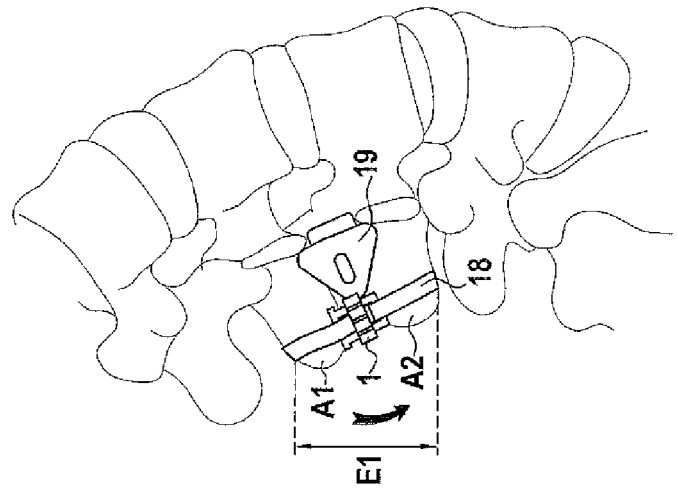
FIGS. 3-5 are schematic views of the intervertebral holding device shown in FIG. 2 in different positions of the vertebral column: in natural curvature (FIG. 3), in flexure (FIG. 4) and in extension (FIG. 5).

FIG. 3 shows the holding device 1 in the natural spinal curvature position with an intervertebral support device 19, in this particular example a wedge 19. The distance E maintained between the adjoining spinous processes A1, A2 is substantially equal to the maximum spacing E provided by the holding device 1.

Figure 5:
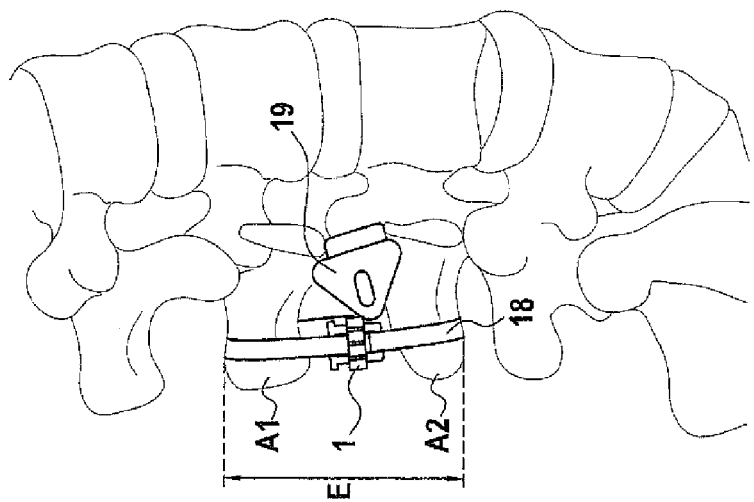

In FIG. 5, the vertebral column being in an extension position, the spinous processes A1 and A2 are closer together and the distance E1 is less than E.

Figure 4:
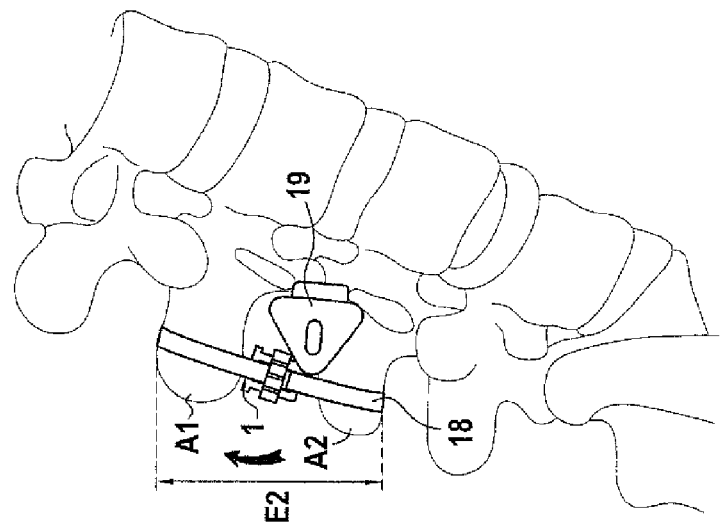

In FIG. 4, when the vertebral column is in flexure, the adjoining spinous processes A1 and A2 draw further apart, putting into tension the holding device 1 which maintains a predetermined maximum intervertebral spacing E2 determined by the surgeon during installation of the device 1.

More precisely, the holding device 1 in this configuration shows an elastic deformation corresponding to a percentage of elastic elongation of the longilineal element.

It should be observed that this detailed description applies to a particular embodiment of the present invention, but that this description does not in any way whatsoever limit the object of the invention; quite the contrary, it has the aim of removing any possible imprecision or any incorrect interpretation of the claims that follow.

The invention claimed is:

1. A holding device adapted for maintaining a predetermined intervertebral spacing comprising a preferably substantially flat, longilineal element, with a predetermined principal width, having a first and a second ends, capable of being positioned around spinous processes, wherein said holding device also comprises:
   a) a rigid support including two lateral portions assembled between front and rear portions, said first end being joined or capable of being joined to said rear portion and said second end remaining free,
   b) a locking element mounted so as to slide on said lateral portions and defining front and rear passage areas with the front and rear portions respectively, allowing passage of said second free end into the rear passage area then into the front passage area while partially surrounding said locking element such that the portion of said longilineal element extending substantially between its first end and the locking element forms a loop with a given perimeter and in that the application of opposite tensions on the inner walls of the loop causes the displacement of said locking element toward said front portion and the locking of the portion of the longilineal element in the front passage area between said locking element and the front portion of the support,
wherein the locking element includes a central opening the inner lateral edges whereof are arranged so as to accommodate the lateral portions of the support and to serve as a guide for the sliding of the locking element on the lateral portions between the front and rear portions of the support.

2. The holding device according to claim 1, wherein the inner distance separating the lateral portions is substantially of the order of the principal width of said longilineal element, or less.

3. The holding device according to claim 1, wherein the front portion of the support is sized and positions with respect to the locking element so as to act as a forward stop for said locking element, the left and right edges of the front portion preferably projecting to either side of the lateral portions act as a stop on the left and right edges of the locking element.

4. The holding device according to claim 1, wherein the upper periphery of the central opening leading toward the front portion is defined by left and right edges and wherein the left edge projects from said upper periphery so that only the left edge of the locking element comes to bear against the front portion of the support providing play between the left edge and the front portion.

5. The holding device according to claim 1, wherein the locking element includes vertical grooves, oriented from the rear portion toward the front portion, reaching to the upper periphery and possibly the lower periphery of the central opening so as to provide clamping teeth on the upper periphery and possibly on the lower periphery.

6. The holding device according to claim 1, wherein the central opening leading toward the front portion of the support comprises teeth shaped like saw teeth along at least one of its left or right edges.

7. The holding device according to claim 1, wherein the inner angular areas of the support defined between the front and/or rear portions and one or the other of the two lateral portions are rounded.

8. The holding device according to claim 1, wherein the support is made of a material selected, alone or in combination among the following materials: stainless steel, titanium, ceramic, polypropylene, polyethylene, high density polyethylene, polyether etherketone (PEEK), chrome-cobalt alloy, PET.

9. The holding device according to claim 1, wherein the longilineal element is obtained by forming multifilament and/or multifilament yarns, by weaving, knitting or braiding, preferably by braiding of multifilament yarns.

10. The holding device according to claim 1, wherein the longilineal element is made of a material selected along or in combination among the following materials: polypropylene, polyethylene terephtalate, polyethylene, high density polyethylene, polyamide 6-6, 4-6 or 12, polyurethane, polyether etherketone (PEEK).

11. The holding device according to claim 1, wherein the longilineal element is a tubular braid the first and second ends whereof are sewn so as to flatten the tubular braid.

12. The holding device according to claim 1, wherein the second end is made in the form of a point and preferably comprises a gripping loop.

13. The holding device according to claim 1, wherein the longilineal element includes a central area positioned between the lateral areas and in that the lateral areas exhibit a lower coefficient of friction than the central area.

14. The holding device according to claim 1, wherein it includes an intervertebral support device, particularly an intervertebral wedge at least the anterior part whereof is capable of being positioned between the over- and underlying laminae respectively of two over- and underlying vertebrae.

15. The holding device according to claim 14, wherein the intervertebral support device comprises at least one attachment means, preferably positioned on one of its lateral walls, for anchoring said longilineal element.

* * * * *